United States Patent
Moine et al.

(10) Patent No.: US 10,702,625 B2
(45) Date of Patent: Jul. 7, 2020

(54) SKIN-ADHESIVE ITEM

(71) Applicant: ELKEM SILICONES FRANCE SAS, Lyons (FR)

(72) Inventors: Caroline Moine, Sorbiers (FR); Maryline Quemin, Villeurbanne (FR)

(73) Assignee: ELKEM SILICONES FRANCE SAS, Lyons (FR)

( * ) Notice: Subject to any disclaimer, the term of this patent is extended or adjusted under 35 U.S.C. 154(b) by 49 days.

(21) Appl. No.: 15/739,093

(22) PCT Filed: Jun. 23, 2016

(86) PCT No.: PCT/FR2016/000105
§ 371 (c)(1),
(2) Date: Dec. 21, 2017

(87) PCT Pub. No.: WO2016/207498
PCT Pub. Date: Dec. 29, 2016

(65) Prior Publication Data
US 2018/0177911 A1 Jun. 28, 2018

(30) Foreign Application Priority Data
Jun. 26, 2015 (FR) ..................... 15 01350

(51) Int. Cl.
| | | |
|---|---|---|
| *C08G 59/68* | (2006.01) | |
| *A61L 15/58* | (2006.01) | |
| *A61L 15/26* | (2006.01) | |
| *A61L 15/28* | (2006.01) | |
| *A61F 13/02* | (2006.01) | |
| *A61F 13/00* | (2006.01) | |

(52) U.S. Cl.
CPC .......... *A61L 15/58* (2013.01); *A61F 13/0246* (2013.01); *A61L 15/26* (2013.01); *A61L 15/28* (2013.01); *A61F 2013/00106* (2013.01); *A61L 2420/02* (2013.01); *A61L 2420/08* (2013.01)

(58) Field of Classification Search
CPC ...... A61L 15/58; A61L 15/26; A61L 2420/08; A61F 13/0246; A61F 2013/00089; C08G 77/12; C08G 77/20
See application file for complete search history.

(56) References Cited

U.S. PATENT DOCUMENTS

| | | |
|---|---|---|
| 2,676,182 A | 4/1954 | Herbert et al. |
| 3,159,601 A | 12/1964 | Ashby |
| 3,159,602 A | 12/1964 | Hamilton et al. |
| 3,220,972 A | 11/1965 | Lamoreaux |
| 3,419,593 A | 12/1968 | Willing |
| 3,508,947 A | 4/1970 | Hughes |
| 3,632,374 A | 1/1972 | Greiller |
| 3,775,452 A | 11/1973 | Karstedt |
| 4,479,987 A | 10/1984 | Koepke et al. |
| 4,699,813 A | 10/1987 | Cavezzan |
| 4,741,966 A | 5/1988 | Cavezzan |
| 4,830,887 A | 5/1989 | Reiter |
| 4,921,704 A | 5/1990 | Fabo |
| 4,974,533 A | 12/1990 | Ishizuka et al. |
| 2016/0009883 A1 | 1/2016 | Pernot |

FOREIGN PATENT DOCUMENTS

| | | | |
|---|---|---|---|
| EP | 0 057 459 | | 8/1982 |
| EP | 0 188 978 | | 7/1986 |
| EP | 0 190 530 | | 8/1986 |
| EP | 0 251 810 | | 1/1988 |
| EP | 0 300 620 | | 1/1989 |
| EP | 0 537 086 | | 4/1993 |
| EP | 0 633 757 | | 1/1995 |
| EP | 0 633 758 | | 10/1996 |
| FR | 2899248 A1 | | 10/2007 |
| WO | 2005/051442 | | 6/2005 |
| WO | 2005054306 | * | 6/2005 |
| WO | 2011/092404 A1 | | 8/2011 |
| WO | 2013096530 | * | 6/2013 |
| WO | 2014/131999 | | 9/2014 |

OTHER PUBLICATIONS

International Search Report dated Aug. 26, 2016, and English Translation of the International Search Report corresponding to International Patent Application No. PCT/FR2016/000105, 6 pages.
"Soft Skin Adhesive Gel for Scar Care and Wound Management HC2 2022 A&B Technical Data Sheet n° SIL 15 037 3—Mar. 2015", XP055268817, Retrieved from the Internet: URL:http://www.silbione.com/wp-content/uploads/2014/01/Silbione HC2 2022 AB SIL150373.pdf [retrieved on Apr. 26, 2016] the whole document, 3 pages.

* cited by examiner

*Primary Examiner* — Kuo Liang Peng
(74) *Attorney, Agent, or Firm* — Dentons US LLP

(57) ABSTRACT

Items that can adhere to the skin for medical or paramedical use are described. Also described, is a skin-adhesive item.

33 Claims, No Drawings

SKIN-ADHESIVE ITEM

CROSS-REFERENCE TO PRIOR APPLICATIONS

This application is a National Stage of PCT/FR2016/000105, filed Jun. 23, 2016, and designating the United States (published on Dec. 29, 2016, as WO 2016/207498 A1), which claims priority under 35 U.S.C. § 119 to French Patent Application No. 1501350, filed Jun. 26, 2015, each hereby expressly incorporated by reference in its entirety and each assigned to the assignee hereof.

The field of the invention is that of items that can adhere to the skin for medical or paramedical use.

The use of silicone gels is very important in the medical field. This is because the intrinsic properties of silicone gels mean that they adhere rapidly to dry skin, but do not stick to the surface of a moist wound, and thus do not cause damage when they are removed. Silicone gels also have the advantage of being able to be assembled to a large number of supports while at the same time being inert for the organism, thus avoiding any problem of toxicity when they are used in human beings. Silicone gels are, inter alia, used for the treatment of wounds or scars since they give the medical device properties that facilitate the recovery of the patient while maintaining a moist environment around the wound and thus making it possible to maintain the hydration of the damaged tissues.

For these applications, the substrate must be biocompatible and flexible and must have good mechanical properties. Polyurethane films are very widely used since they meet all these technical requirements, in particular:
good biocompatibility,
good permeability to water vapor (management of the fluids between the dressing and the external environment so as to prevent the dressing from swelling or from detachment),
good mechanical properties (tensile strength, elongation capacity),
a soft feel, and
good flexibility.

The use of these products involves a step of coating on a substrate. The coating of silicone gels on these polyurethane supports is a key step of the process for producing the medical device and the properties of this composite must be good. Indeed, the gel must be sufficiently adhesive to the skin to keep the device in place. It must also adhere sufficiently to the substrate to avoid the production of residues when the device is removed.

However, it is known that the adhesion of silicone gels on plastic supports having a low surface energy is difficult to obtain. However, adhesion to the substrate is fundamental for ensuring good cohesion of the adhesive item to the skin, in particular for medical or paramedical use, and avoiding the presence of residues when the item is removed.

Thus, when silicone gels are used as polyurethane support-coating elements or as a layer affixed to these supports, it is desirable to reinforce their adhesion to the polyurethane supports, in such a way that the products thus treated withstand physical stresses efficiently.

It is, for example, known that the adhesion of silicone gels to a plastic substrate is improved by applying, to the surface of the support, a Corona treatment in order to modify the surface energy of said support. This technique consists in oxidizing the surface of the material in order to improve the wettability by increasing the surface tension. However, the level of adherence obtained is not always sufficient for some applications.

Another approach for improving the adherence of silicone gels to plastic supports, for example polyurethane supports, consists in using an adhesion primer, also known as a "tie primer". This technical approach makes it possible to obtain products which offer a slightly improved level of attachment compared with a polymer substrate subjected to a Corona treatment. Among the primers that exist at the current time, mention may be made of:

the primers formulated in a solvent environment. One example is described in patent application WO2011/092404 from the company Bluestar Silicones France, wherein a primer consists of an active material (organopolysiloxane oil comprising a hydrosilyl function (SiH) and Si-alkenyl or a silicone resin having hydrosilyl functions) diluted in a silicone solvent (cyclopentasiloxane).This primer is very effective but must be used under very precise conditions (dilution of active material, weight of primer coated) so that a good compromise of properties (adhesion to the substrate and preservation of the tack) is achieved. Furthermore, another drawback of this type of primer is its solvent content, which makes it more difficult to use during the coating step; and silicone elastomer primers which are prepared from precursor compositions which crosslink via a hydrosilylation reaction comprising adhesion promoters which are usually silanes that make it possible to improve the adhesion on various substrates (polyamide, polyester or polyurethane substrates). However, during the preparation of the silicone elastomer, the condensation of the silanes releases by-products (alcohols) which make this type of primer more difficult to use during the coating step.

According to another technical approach, for example described in patent application WO 2005/051442 from the company Dow Corning Corp., the adherence of a silicone gel to the surface of a plastic polymer substrate, such as polyurethane films, is improved by directly treating the substrate or the silicone gel by bringing it into contact with derivatives: titanate, zirconate, siloxanes having hydrosilyl functions or platinum, such as a platinum-(0)-1,3-diethenyl-1,1,3,3-tetramethyldisiloxane complex. It should be noted that the use of adhesion primers of titanate type, such as titanium tetrabutanoate, is very widespread but poses problems during the processing thereof.

A solution to the problem stated above is set out in patent application WO 2014/131999 from the company Urgo which describes an item comprising at least one polymer substrate assembled to at least one silicone polymer layer, characterized in that at least one of the polymer substrate or of the silicone polymer layer has been brought into contact with particles of titanium dioxide, of magnesium oxide and/or of zinc oxide, before assembly of said item, and in that at least one of the polymer substrate or of the silicone polymer layer has been brought into contact with water before or after assembly of said item. The adhesion results show a clear improvement compared with a Corona treatment or with the impregnation of a nonwoven support based on polyethylene impregnated with titanium tetrabutanoate at 5% by weight in isopropanol.

It is also possible to use other types of adhesion primers formulated in an aqueous phase, but the results in terms of adhesion improvement are not satisfactory, and it also requires the incorporation of additives (for example of acetic acid) during the processing thereof and/or the application of a heat treatment, said treatment being incompatible with the use of certain polymer substrates.

Thus, the use of adhesion primers of various types, and in particular of titanate type, causes a good number of problems or complications associated with the processing thereof and with the use thereof. In addition, the adhesion levels obtained by virtue of these treatments still need to be improved. The applicant has thus sought to develop a novel adhesion primer which offers improved adhesion between a silicone gel and a flexible polyurethane film not using adhesion promoters of titanate or silane type, or even solvent, and offering the best possible guarantees in terms of health safety.

Thus, the object of the present invention is to provide novel items that can adhere to the skin, comprising a polyurethane support coated with a specific primer and a silicone polymer layer which is in the form of silicone gel, in which the adherence of the silicone to the polyurethane support is particularly high, said substrates being suitable, moreover, to medical, paramedical or cosmetic applications without causing problems of toxicity associated with the use of certain solvents, silanes or titanates.

Another objective of the present invention is to provide novel items that can adhere to the skin, which can be used as a layer of contact with the skin in various types of dressings or medical devices.

Another objective of the present invention consists in providing novel items that can adhere to the skin, in which the tack properties of the silicone gel are sufficient to enable good adhesion to the skin.

Another objective of the present invention is to provide a process for preparing said skin-adhesive item.

These objectives are achieved by means of the invention which relates to a skin-adhesive item comprising:
- a support S which is a flexible polyurethane film having a top face S1 and a bottom face S2,
- at least one tie primer C1 applied to at least one part or to all of the top face S1 of said support S,
- at least one layer D1 made up of a silicone gel E obtained by crosslinking a crosslinkable silicone composition Y by means of a hydrosilylation reaction, which has been applied to said tie primer C1 facing said support S, and
- optionally at least one protective layer F consisting of a peel-off protective material and applied to said layer D1, said tie primer C1 being characterized in that it consists of a silicone elastomer which is not a silicone gel and which is obtained by crosslinking a silicone composition X consisting of:
1) at least one organopolysiloxane A comprising, per molecule, at least two vinyl radicals each bonded to a silicon atom and consisting:
   (i) of at least two siloxy units of formula (A1):

$$Y_aZ_bSiO_{(4-(a+b))/2} \qquad (A1)$$

wherein:
   Y represents a $C_2$ to $C_6$ alkenyl group, and preferably a vinyl group,
   Z represents a monovalent hydrocarbon-based group chosen from alkyl groups having from 1 to 8 carbon atoms inclusive, such as methyl, ethyl, propyl and 3,3,3-trifluoropropyl groups, cycloalkyl groups, such as cyclohexyl, cycloheptyl and cyclooctyl groups, and aryl groups such as xylyl, tolyl and phenyl groups, a and b represent integers, a being 1, 2 or 3, b being 0, 1 or 2 and (a+b) being 1, 2 or 3;
   (ii) and optionally comprising other siloxy units of formula (A2):

$$Z_cSiO_{(4-c)/2} \qquad (A2)$$

wherein:
   Z has the same meaning as above, and
   c represents an integer which is 0, 1, 2 or 3;
2) at least one organopolysiloxane B comprising, per molecule, at least three hydrogen atoms each bonded to a silicon atom and consisting:
   (i) of least three siloxy units of formula (B1):

$$HZ_bSiO_{(3-b)/2} \qquad (B1)$$

wherein:
   H is a hydrogen atom,
   Z represents a monovalent hydrocarbon-based group chosen from alkyl groups having from 1 to 8 carbon atoms inclusive, such as methyl, ethyl, propyl and 3,3,3-trifluoropropyl groups, cycloalkyl groups, such as cyclohexyl, cycloheptyl and cyclooctyl groups, and aryl groups such as xylyl, tolyl and phenyl groups,
   b is 0, 1 or 2;
   (ii) and optionally comprising other siloxy units of formula (B2):

$$Z_cSiO_{(4-c)/2} \qquad (B2)$$

wherein:
   Z has the same meaning as above, and
   c represents an integer which is 0, 1, 2, or 3;
3) at least one hydrosilylation catalyst C;
4) at least one hydrosilylation reaction inhibitor D;
5) optionally at least one stabilizing additive K; and
7) optionally at least one silicone resin M which has hydroxyl groups and is free of alkenyl or hydrosilyl SiH groups, and
with the proviso that the amounts by weight of the organopolysiloxanes A and B are determined such that the RHalk=nH/tAlk ratio is 1.00≤RHalk≤4.5 with:
   nH=number of moles of hydrogen atom directly bonded to a silicon atom of the organopolysiloxane B, and
   tAlk=number of moles of alkenyl directly bonded to a silicon atom of the organopolysiloxane A.

The applicant has implemented considerable research means and numerous experiments to achieve this objective among others. Furthermore, at the end of this, it has to its credit found, entirely surprisingly and unexpectedly, that using a tie primer according to the invention on a flexible polyurethane plastic film with low surface energy makes it possible to obtain satisfactory adhesion when a silicone gel is then coated on said primer.

This is all the more surprising since the silicone composition X according to the invention is free of titanate, of bifunctional silicone or of silane which are presented by the prior art as being components essential for this type of desired adhesion.

The absence of titanate or bifunctional silicone, such as those presented in patent application WO 2011/092404, in the silicone composition X according to the invention makes it possible to dispense with using organic solvent, thus avoiding a large number of problems of intolerance or even toxicity associated with the use of organic solvents in the production of an item for medical use. This aspect is the subject of most particular attention from the industry producing dressings for medical or paramedical use.

The absence of silane in the silicone composition X makes it possible to avoid the release of alcohol due to the condensation of the silanes which is an advantage during the production of the coated supports.

Another advantage linked to the use, as tie primer, of a silicone elastomer obtained by crosslinking a silicone composition X according to the invention is that the tack of the silicone gel coated onto the primer according to the invention is not degraded. The term "tack", or "instantaneous tackiness", determines the adhesive capacity at short times. In order to assess and evaluate the tack, "Probe Tack" methods have been developed. The principle of these tests consists in bringing the surface of a rigid metal punch into contact with the silicone gel and in recording the change in the force during the separation step. The integration of the curve representing the force as a function of the displacement of the punch gives the tack energy (unit in mJ/cm$^2$).

For the purposes of the present invention, the expression "silicone gel" denotes a crosslinked silicone product which exhibits no flow when it is in the stable state and is characterized by a degree of penetration (or "penetrability") of between 80 and 300 tenths of 1 mm. It is measured by penetrometry according to standard NF ISO 2137, using a Petrotest penetrometer, model PNR 12, with a total weight of the rod and of the cone fixed at 62.5 g. The cone-penetrability of a silicone gel is determined at 25° C. by measuring the depth of penetration of the cone into the sample, said penetrability being obtained by releasing the cone assembly of the penetrometer and leaving the cone to act for 5 seconds.

Preferably, the amounts of the silicone composition X applied to the support S will be determined so as to obtain coatings having a content of silicone composition X before crosslinking of between 1 and 100 g/m$^2$ of support, preferably between 1 and 50 g/m$^2$ and even more preferentially between 2 and 30 g/m$^2$.

According to one advantageous embodiment, the amounts by weight of the organopolysiloxanes A and B are determined in such a way that 1.50≤RHalk≤4.0. Preferably, the amounts by weight of the organopolysiloxanes A and B are determined such that 1.50≤RHalk≤2.5.

The organopolysiloxane A can have a linear, branched, cyclic or network structure. When it is a question of linear polyorganosiloxanes, they can essentially consist:
of siloxyl units "D" chosen from the units of formulae $R_2SiO_{2/2}$, $RZSiO_{2/2}$ and $Z_2SiO_{2/2}$;
of siloxyl units "M" chosen from the units of formulae $R_3SiO_{1/2}$, $R_2ZSiO_{1/2}$, $RZ_2SiO_{1/2}$ and $R_3SiO_{2/2}$.
the symbol Z represents a $C_2$ to $C_6$ alkenyl group, and preferably a vinyl group, and the symbol R represents a monovalent hydrocarbon-based group chosen from alkyl groups having from 1 to 8 carbon atoms inclusive, such as methyl, ethyl, propyl and 3,3,3-trifluoropropyl groups, cycloalkyl groups, such as cyclohexyl, cycloheptyl and cyclooctyl groups, and aryl groups such as xylyl, tolyl and phenyl groups.

By way of examples of units "D", mention may be made of dimethylsiloxy, methylphenylsiloxy, methylvinylsiloxy, methylbutenylsiloxy, methylhexenylsiloxy, methyldecenylsiloxy and methyldecadienylsiloxy groups.

By way of example of units "M", mention may be made of trimethylsiloxy, dimethylphenylsiloxy, dimethylvinylsiloxy and dimethylhexenylsiloxy groups.

These organopolysiloxanes, in particular when they are linear, can be oils having a dynamic viscosity at 25° C. of between 1 mPa·s and 100 000 mPa·s, preferentially between 10 mPa·s and 10 000 mPa·s and even more preferentially between 50 mPa·s and 5000 mPa·s.

All the viscosities to which reference is made in the present disclosure correspond to a magnitude of dynamic viscosity at 25° C. termed "Newtonian", that is to say the dynamic viscosity which is measured, in a manner known per se, with a Brookfield viscometer at a shear rate gradient which is sufficiently low for the viscosity measured to be independent of the shear rate gradient.

When it is a question of a cyclic organopolysiloxane, the latter can consist of siloxyl units "D" chosen from the units of formulae $R_2SiO_{2/2}$, $RZSiO_{2/2}$ and $Z_2SiO_{2/2}$, R and Z having the same meanings as above. Examples of such units "D" are described above. This cyclic polyorganosiloxane can have a dynamic viscosity at 25° C. of between 1 mPa·s and 5000 mPa·s.

Examples of organopolysiloxane A are:
polydimethylsiloxanes with dimethylvinylsilyl end groups;
poly(methylphenylsiloxane-co-dimethylsiloxane)s with dimethylvinylsilyl end groups;
poly(vinylmethylsiloxane-co-dimethylsiloxane)s with dimethylvinylsilyl end groups;
poly(dimethylsiloxane-co-vinylmethylsiloxane)s with trimethylsilyl end groups;
cyclic polymethylvinylsiloxanes.

The organopolysiloxane B comprises, per molecule, at least three hydrogen atoms each bonded to a silicon atom and consists:
(i) of at least three siloxy units of formula (B1):

$$HZ_bSiO_{(3-b)/2} \quad (B1)$$

wherein:
H is a hydrogen atom,
Z represents a monovalent hydrocarbon-based group chosen from alkyl groups having from 1 to 8 carbon atoms inclusive, such as methyl, ethyl, propyl and 3,3,3-trifluoropropyl groups, cycloalkyl groups, such as cyclohexyl, cycloheptyl and cyclooctyl groups, and aryl groups such as xylyl, tolyl and phenyl groups,
b being 0, 1 or 2;
(ii) and optionally comprises other siloxy units of formula (B2):

$$Z_cSiO_{(4-c)/2} \quad (B2)$$

wherein:
Z has the same meaning as above, and c represents an integer which is 0, 1, 2 or 3.

Examples of units of formula (B1) are the following: $H(CH_3)_2SiO_{1/2}$, $HCH_3SiO_{2/2}$ and $HSiO_{3/2}$.

The organopolysiloxane B can have a linear, branched, cyclic or network structure. When it is a question of linear polyorganosiloxanes, they can essentially consist:
of siloxyl units "D" chosen from the units of formulae $HZSiO_{2/2}$ and $Z_2SiO_{2/2}$;
of siloxyl units "M" chosen from the units of formulae $HZ_2SiO_{1/2}$ and $Z_3SiO_{2/2}$,
with the symbol Z having the same meaning as above and the symbol H denoting a hydrogen atom.

These linear polyorganosiloxanes can be oils having a dynamic viscosity at 25° C. of between 1 mPa·s and 100 000 mPa·s, preferentially between 1 mPa·s and 5000 mPa·s, and even more preferentially between 1 mPa·s and 2000 mPa·s.

When it is a question of cyclic polyorganosiloxanes, they can consist of siloxyl units "D" chosen from the units of formula $Z_2SiO_{2/2}$ and siloxyl units of formula $HZSiO_{2/2}$ only. Z has the same meaning as above. These cyclic polyorganosiloxanes can have a dynamic viscosity at 25° C. of between 1 mPa·s and 5000 mPa·s.

Examples of organopolysiloxane B are:
polydimethylsiloxanes with hydrodimethylsilyl end groups;
poly(dimethylsiloxane-co-methylhydrosiloxane)s with trimethylsilyl end groups;
poly(dimethylsiloxane-co-methylhydrosiloxane)s with hydrodimethylsilyl end groups;
poly(methylhydrosiloxane)s with trimethylsilyl end groups;
cyclic poly(methylhydrosiloxane)s.

When it is a question of branched or network polyorganosiloxanes, they can also comprise:
siloxyl units "T" chosen from the units of formulae $HSiO_{3/2}$ and $ZSiO_{3/2}$;
siloxyl units "Q" of formula $SiO_{4/2}$;
with the symbol H representing a hydrogen atom and Z having the same meaning as above.

As hydrosilylation catalyst C that is of use according to the invention, mention may be made of the compounds of a metal belonging to the platinum group well known to those skilled in the art. The metals of the platinum group are those known as platinoids, a name which groups together, in addition to platinum, ruthenium, rhodium, palladium, osmium and iridium. Platinum and rhodium compounds are preferably used. Use may in particular be made of the complexes of platinum and of an organic product described in U.S. Pat. Nos. 3,159,601, 3,159,602, 3,220,972 and European patents EP-A-0 057 459, EP-A-0 188 978 and EP-A-0 190 530, and the complexes of platinum and of vinylorganosiloxanes described in U.S. Pat. No. 3,419,593. The catalyst that is generally preferred is platinum. By way of examples, mention may be made of platinum black, chloroplatinic acid, an alcohol-modified chloroplatinic acid, a complex of chloroplatinic acid with an olefin, an aldehyde, a vinylsiloxane or an acetylenic alcohol, inter alia. Preference is given to the Karstedt solution or complex, as described in U.S. Pat. No. 3,775,452, to chloroplatinic acid hexahydrate or a platinum catalyst comprising carbene ligands.

As hydrosilylation reaction inhibitor D that is of use according to the invention, mention may be made of that chosen from α-acetylenic alcohols, α,α'-acetylenic diesters, ene-yne conjugated compounds, α-acetylenic ketones, acrylonitriles, maleates, fumarates and mixtures thereof. These compounds capable of performing the function of hydrosilylation inhibitor are well known to those skilled in the art. They can be used alone or as mixtures.

An inhibitor D of α-acetylenic alcohol type can be chosen from the compounds of formula (D1) below:

$$(R^1)(R^2)C(OH)—C≡CH \quad (D1)$$

wherein:
the $R^1$ group represents an alkyl group, a cycloalkyl group, a (cycloalkyl)alkyl group, an aryl group or an arylalkyl group,
the $R^2$ group represents a hydrogen atom, an alkyl group, a cycloalkyl group, a (cycloalkyl)alkyl group, an aryl group or an arylalkyl group,
or else $R^1$ and $R^2$ constitute, together with the carbon atom to which they are bonded, a 5-, 6-, 7- or 8-membered aliphatic ring which is optionally substituted one or more times.

According to formula (D1):
the term "alkyl" is intended to mean a saturated hydrocarbon-based chain containing from 1 to 20 carbon atoms, preferably from 1 to 8 carbon atoms. An alkyl group can be chosen from the group made up of methyl, ethyl, isopropyl, n-propyl, tert-butyl, isobutyl, n-butyl, n-pentyl, isoamyl and 1,1-dimethylpropyl;
the term "cycloalkyl" is intended to mean, according to the invention, a monocyclic or polycyclic, preferably monocyclic or bicyclic, saturated hydrocarbon-based group containing from 3 to 20 carbon atoms, preferably from 5 to 8 carbon atoms. When the cycloalkyl group is polycyclic, the multiple cyclic nuclei can be attached to one another by a covalent bond and/or by a spirane atom and/or can be fused to one another. A cycloalkyl group can be chosen from the group made up of cyclopropyl, cyclobutyl, cyclopentyl, cyclohexyl, cycloheptyl, cyclooctyl, adamantane and norborane;
the term "(cycloalkyl)alkyl" is intended to mean, according to the invention, a cycloalkyl group as defined above bonded to an alkyl group also as defined above;
the term "aryl" is intended to mean, according to the invention, a monocyclic or polycyclic, aromatic hydrocarbon-based group containing from 5 to 18 carbon atoms. An aryl group can be chosen from the group made up of phenyl, naphthyl, anthracenyl and phenanthryl;
the term "arylalkyl" is intended to mean, according to the invention, an aryl group as defined above bonded to an alkyl group also as defined above.

According to one preferred embodiment, in formula (D1), $R^1$ and $R^2$ constitute, together with the carbon atom to which they are bonded, a 5-, 6-, 7- or 8-membered, unsubstituted aliphatic ring. According to another preferred embodiment, $R^1$ and $R^2$, which may be identical or different, represent, independently of one another, a $C_1$ to $C_{12}$, preferably $C_1$ to $C_6$, monovalent alkyl group.

An inhibitor D which is an α-acetylenic alcohol which is of use according to the invention can be chosen from the group made up of the following compounds: 1-ethynyl-1-cyclopentanol; 1-ethynyl-1-cyclohexanol (also called ECH); 1-ethynyl-1-cycloheptanol; 1-ethynyl-1-cyclooctanol; 3-methyl-1-butyn-3-ol (also called MBT); 3-methyl-1-pentyn-3-ol; 3-methyl-1-hexyn-3-ol; 3-methyl-1-heptyn-3-ol; 3-methyl-1-octyn-3-ol; 3-methyl-1-nonyn-3-ol; 3-methyl-1-decyn-3-ol; 3-methyl-1-dodecyn-3-ol; 3-methyl-1-pentadecyn-3-ol; 3-ethyl-1-pentyn-3-ol; 3-ethyl-1-hexyn-3-ol; 3-ethyl-1-heptyn-3-ol; 3,5-dimethyl-1-hexyn-3-ol; 3-isobutyl-5-methyl-1-hexyn-3-ol; 3,4,4-trimethyl-1-pentyn-3-ol; 3-ethyl-5-methyl-1-heptyn-3-ol; 3,6-diethyl-1-nonyn-3-ol; 3,7,11-trimethyl-1-dodecyn-3-ol (also called TMDDO); 1,1-diphenyl-2-propyn-1-ol; 3-butyn-2-ol; 1-pentyn-3-ol; 1-hexyn-3-ol; 1-heptyn-3-ol; 5-methyl-1-hexyn-3-ol; 4-ethyl-1-octyn-3-ol and 9-ethynyl-9-fluorenol.

An inhibitor D of a, a'-acetylenic diester type can be chosen from the compounds of formula (D2) below:

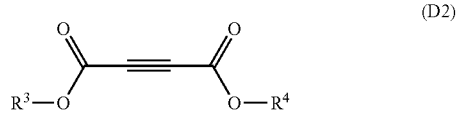

wherein the R3 and R4 groups, which may be identical or different, represent, independently of one another, an alkyl group, a cycloalkyl group, a (cycloalkyl)alkyl group, an aryl group, an arylalkyl group or a silyl group.

The term "silyl" is intended to mean, according to the invention, a group of formula —SiR$_3$, each R independently representing an alkyl group containing from 1 to 20 carbon atoms, preferably from 1 to 8 carbon atoms. A silyl group can be, for example, the trimethylsilyl group.

According to one particular embodiment, in formula (D2), R$^3$ and R$^4$, which may be identical or different, represent, independently of one another, a C$_1$ to C$_{12}$, preferably C$_1$ to C$_6$ alkyl group, or the trimethylsilyl group. An inhibitor D which is an α,α'-acetylenic diester that is of use according to the invention can be chosen from the group made up of the following compounds: dimethyl acetylenedicarboxylate (DMAD), diethyl acetylenedicarboxylate, tert-butyl acetylenedicarboxylate and bis(trimethylsilyl) acetylenedicarboxylate.

An inhibitor D of ene-yne conjugated compound type can be chosen from the compounds of formula (D3) below:

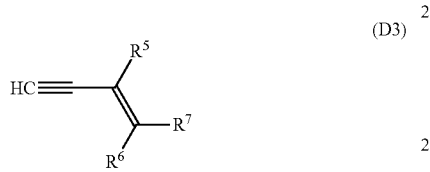

(D3)

wherein:
the R$^5$, R$^6$ and R$^7$ groups represent, independently of one another, a hydrogen atom, an alkyl group, a cycloalkyl group, a (cycloalkyl)alkyl group, an aryl group or an arylalkyl group,
or else at least two groups among the R$^5$, R$^6$ and R$^7$ groups constitute, together with the carbon atom(s) to which they are bonded, a 5-, 6-, 7- or 8-membered aliphatic ring which is optionally substituted one or more times.

According to one particular embodiment, the R$^5$, R$^6$ and R$^7$ groups represent, independently of one another, a hydrogen atom, a C$_1$ to C$_{12}$, preferably C$_1$ to C$_6$, alkyl group or an aryl group. An inhibitor D which is an ene-yne conjugated compound which is of use according to the invention can be chosen from the group made up of the following compounds: 3-methyl-3-penten-1-yne; 3-methyl-3-hexen-1-yne; 2,5-dimethyl-3-hexen-1-yne; 3-ethyl-3-buten-1-yne; and 3-phenyl-3-buten-1-yne. According to another particular embodiment, two groups chosen from the R$^5$, R$^6$ and R$^7$ groups constitute, together with the carbon atom(s) to which they are bonded, a 5-, 6-, 7- or 8-membered unsubstituted aliphatic ring and the remaining third group represents a hydrogen atom or a C$_1$ to C$_{12}$, preferably C$_1$ to C$_6$, alkyl group. An inhibitor D which is an ene-yne conjugated compound that is of use according to the invention can be 1-ethynyl-1-cyclohexene.

An inhibitor D of a-acetylenic ketone type can be chosen from the compounds of formula (D4) below:

(D2)

wherein R$^8$ represents an alkyl group, a cycloalkyl group, a (cycloalkyl)alkyl group, an aryl group or an arylalkyl group, the alkyl, cycloalkyl, (cycloalkyl)alkyl, aryl or arylalkyl groups possibly optionally being substituted one or more times with a chlorine, bromine or iodine atom.

According to one preferred embodiment, R$^8$ represents a C$_1$ to C$_{12}$, preferably C$_1$ to C$_6$, monovalent alkyl group which is optionally substituted one or more times with a chlorine or bromine atom, or a cycloalkyl group, or an aryl group. An inhibitor D which is an α-acetylenic ketone that is of use according to the invention can be chosen from the group consisting of the following compounds: 1-octyn-3-one, 8-chloro-1-octyn-3-one; 8-bromo-1-octyn-3-one; 4,4-dimethyl-1-octyn-3-one; 7-chloro-1-heptyn-3-one; 1-hexyn-3-one; 1-pentyn-3-one; 4-methyl-1-pentyn-3-one; 4,4-dimethyl-1-pentyn-3-one; 1-cyclohexyl-1-propyn-3-one; benzoacetylene and o-chlorobenzoylacetylene.

An inhibitor D of acrylonitrile type can be chosen from the compounds of formula (D5) below:

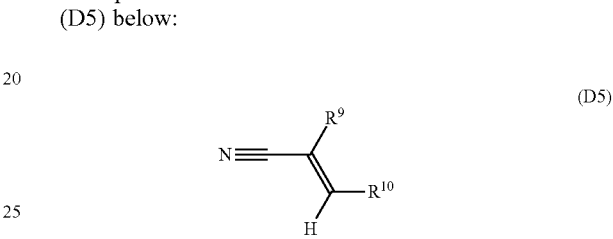

(D5)

wherein R$^9$ and R$^{10}$ represent, independently of one another, a hydrogen atom, a chlorine, bromine or iodine atom, an alkyl group, a cycloalkyl group, a (cycloalkyl)alkyl group, an aryl group or an arylalkyl group, the alkyl, cycloalkyl, (cycloalkyl)alkyl, aryl or arylalkyl groups possibly optionally being substituted one or more times with a chlorine, bromine or iodine atom. An inhibitor D which is an acrylonitrile that is of use according to the invention can be chosen from the group consisting of the following compounds: acrylonitrile; methacrylonitrile; 2-chloroacrylonitryl; crotononitrile and cinnamonitrile.

An inhibitor D of maleate or fumarate type can be chosen from the compounds of formulae (D6) and (D7) below:

(D6)

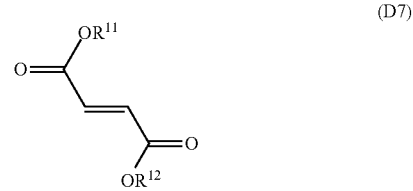

(D7)

wherein R$^{11}$ and R$^{12}$, which may be identical or different, represent, independently of one another, an alkyl or alkenyl group, a cycloalkyl group, a (cycloalkyl)alkyl group, an aryl group or an arylalkyl group, said alkyl, alkenyl, cycloalkyl, (cycloalkyl)alkyl, aryl and arylalkyl groups possibly being substituted with an alkoxy group.

The term "alkenyl" is intended to mean, according to the invention, a saturated hydrocarbon-based chain containing from 1 to 20 carbon atoms, preferably from 1 to 8 carbon atoms, comprising at least one double unsaturation. An alkenyl group can be chosen from the group made up of vinyl or allyl.

The term "alkoxy" is intended to mean, according to formula (D6) or (D7), an alkyl group as defined above bonded to an oxygen atom. An alkoxy group can be chosen from the group made up of methoxy, ethoxy, propoxy and butoxy.

According to one particular embodiment, $R^{11}$ and $R^{12}$, which may be identical or different, represent, independently of one another, a $C_1$ to $C_{12}$, preferably $C_1$ to $C_6$, alkyl or alkenyl group which is optionally substituted with a $C_1$ to $C_6$ alkoxy group.

An inhibitor D which is a maleate or a fumarate that is of use according to the invention can be chosen from the group made up of diethyl fumarate, diethyl maleate diallyl fumarate, diallyl maleate and bis(methoxyisopropyl) maleate.

Inhibitors D chosen from α-acetylenic alcohols, α,α'-acetylenic diesters, ene-yne conjugated compounds, α-acetylenic ketones, acrylonitriles, maleates and fumarates are commercially available. Mention may in particular be made of ECH (1-ethynyl-1-cyclohexanol) which is commercially available from BASF, dimethyl maleate which is commercially available from DMS and dimethyl acetylenedicarboxylate which is available from City Chemical LLC.

These inhibitors are added in an amount by weight of between 1 and 50 000 ppm relative to the weight of the total silicone composition, in particular between 10 and 10 000 ppm, preferably between 20 and 2000 ppm and even more preferentially between 20 ppm and 500 ppm.

As an example of a stabilizing additive K, mention may for example be made of silylated derivatives of phosphoric acid.

Preferably, the nonfunctionalized organopolysiloxane I is linear or substantially linear and has a dynamic viscosity of less than or equal to 50 000 mPa·s, preferably of between 20 and 40 000 mPa·s.

According to another particularly advantageous embodiment, the silicone composition X contains at least two organopolysiloxanes A according to the invention and is characterized in that at least one is a silicone resin A1 consisting:

(i) of at least two siloxy units of formula (A1):

wherein:
Y represents a $C_2$ to $C_6$ alkenyl group, and preferably a vinyl group,
Z represents a monovalent hydrocarbon-based group chosen from alkyl groups having from 1 to 8 carbon atoms inclusive, such as methyl, ethyl, propyl and 3,3,3-trifluoropropyl groups, cycloalkyl groups, such as cyclohexyl, cycloheptyl and cyclooctyl groups, and aryl groups such as xylyl, tolyl and phenyl groups,
a and b represent integers, a being 1, 2 or 3, b being 0, 1 or 2 and (a+b) being 1, 2 or 3; and preferably a=1;

(ii) and other siloxy units of formula (A2):

wherein:
Z has the same meaning as above,
c represents an integer which is 0, 1, 2 or 3, and
with the proviso that at least one siloxy unit (A2) has the formula $SiO_{4/2}$.

The silicone resin A1 is a well-known and commercially available branched organopolysiloxane oligomer or polymer. It is used in diluted form, preferably diluted in a silicone oil which can bear vinyl functions. In this case, the choice of the silicone oil will be made so as to have a dynamic viscosity at 25° C. of between 1000 mPa·s and 100 000 mPa·s. As examples of branched organopolysiloxane oligomers or polymers, mention may be made of the "MQ" resins, the "MDQ" resins, the "TD" resins and the "MDT" resins, the alkenyl functions being borne by the siloxyl units M, D and/or T. Those skilled in the art in the silicone field commonly use this nomenclature which represents the siloxyl units below:

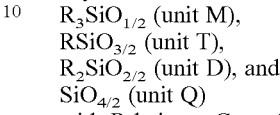

$R_3SiO_{1/2}$ (unit M),
$RSiO_{3/2}$ (unit T),
$R_2SiO_{2/2}$ (unit D), and
$SiO_{4/2}$ (unit Q)

with R being a $C_2$ to $C_6$ alkenyl group and preferably a vinyl or a monovalent hydrocarbon-based group chosen from alkyl groups having from 1 to 8 carbon atoms inclusive, such as methyl, ethyl, propyl and 3,3,3-trifluoropropyl groups, cycloalkyl groups, such as cyclohexyl, cycloheptyl and cyclooctyl groups, and aryl groups such as xylyl, tolyl and phenyl groups.

The silicone resin A1 that is particularly of use according to the invention is a silicone resin comprising "Si-alkenyl" functions, that is to say resins comprising vinyl, allyl and/or hexenyl functions. Advantageously, they comprise, in the structure thereof, from 0.1% to 20% by weight of alkenyl group(s). In this resin, the alkenyl groups can be located on siloxyl units M, D or T. These resins can be prepared for example according to the process described in U.S. Pat. No. 2,676,182. A certain number of these resins are commercially available, most commonly in the "solutions" state, for example in xylene.

For example, the silicone resin A1 can comprise:
at least two different siloxyl units chosen from those of formulae (I) and (II) below:

wherein:
the symbols W, which may be identical or different, each represent a $C_2$-$C_6$ alkenyl group; preferably a vinyl, allyl and/or hexenyl group and even more preferentially a vinyl group,
the symbols Z', which may be identical or different, each represent a monovalent hydrocarbon-based group chosen from alkyl groups having from 1 to 8 carbon atoms inclusive, such as methyl, ethyl, propyl and 3,3,3-trifluoropropyl groups, cycloalkyl groups such as cyclohexyl, cycloheptyl and cyclooctyl groups, and aryl groups such as xylyl, tolyl and phenyl groups, and
the symbol a is equal to 1 or 2, preferably 1, the symbol b is equal to 0, 1 or 2 and the sum a+b is equal to 1, 2 or 3,
and optionally units of formula below:

wherein Z' has the same meaning as above and the symbol c is equal to 0, 1, 2 or 3, and
with the proviso that at least one of the units (I) or (II) is a unit T or Q.

The term "unit T" is intended to mean a siloxyl unit of formula $RSiO_{3/2}$ and the term "unit Q" is intended to mean a siloxyl unit of formula $SiO_{4/2}$, and the R groups are as defined below.

In one preferred embodiment of the invention, the silicone resin A1 is chosen from the group made up of the following silicone resins:

MD$^{Vi}$Q wherein the vinyl groups are included in the units D,

MD$^{Vi}$TQ wherein the vinyl groups are included in the units D,

MM$^{Vi}$Q wherein the vinyl groups are included in a part of the units M,

MM$^{Vi}$TQ wherein the vinyl groups are included in a part of the units M,

MM$^{Vi}$DD$^{Vi}$Q wherein the vinyl groups are included in the units M and D, and mixtures thereof, with:

M=siloxyl unit of formula $R_3SiO_{1/2}$

M$^{Vi}$=siloxyl unit of formula $(R_2)(vinyl)SiO_{1/2}$

D=siloxyl unit of formula $R_2SiO_{2/2}$

D$^{Vi}$=siloxyl unit of formula $(R)(vinyl)SiO_{2/2}$

Q=siloxyl unit of formula $SiO_{4/2}$;

T=siloxyl unit of formula $RSiO_{3/2}$, and the R groups, which may be identical or different, are monovalent hydrocarbon-based groups chosen from alkyl groups having from 1 to 8 carbon atoms inclusive, such as methyl, ethyl, propyl and 3,3,3-trifluoropropyl groups, cycloalkyl groups, such as cyclohexyl, cycloheptyl and cyclooctyl groups, and aryl groups such as xylyl, tolyl and phenyl groups.

According to another particular embodiment of the invention, the silicone resin A1 is added to the composition according to the invention in the form of a mixture in at least one organopolysiloxane oil, for example corresponding to the definition of the organopolysiloxane A described above, or in at least one hydrocarbon-based solvent such as toluene, xylene or derivatives known as Exxsol® and sold by the company Exxon Mobil.

Preferably, the silicone resin A1 comprising at least two $C_2$ to $C_6$ alkenyl radicals each bonded to a silicon atom has the formula MD$^{Vi}$Q wherein:

M is a monovalent siloxyl unit of formula $R_3SiO_{1/2}$

D$^{Vi}$ is a divalent siloxyl unit of formula $RXSiO_{2/2}$, and

Q is a tetravalent siloxyl unit of formula $SiO_{4/2}$, with the radical X corresponding to an alkenyl group having from 2 to 6 carbon atoms, preferably a vinyl group, and the radical R corresponding to a monovalent hydrocarbon-based group chosen from alkyl groups having from 1 to 8 carbon atoms inclusive, such as methyl, ethyl, propyl and 3,3,3-trifluoropropyl groups, cycloalkyl groups, such as cyclohexyl, cycloheptyl and cyclooctyl groups, and aryl groups such as xylyl, tolyl and phenyl groups.

According to another embodiment of the invention, the silicone resin A1 is present in the composition X up to 90% by weight relative to the total weight of the composition X, preferably between 10% and 90% by weight relative to the total weight of the composition X and even more preferably between 30% and 70% by weight relative to the total weight of the composition X. For optimal use, the silicone resin A1 is present in the composition X between 40% and 60% by weight relative to the total weight of the composition X.

As examples of silicone resin M mention may be made of those which have:

at least two different siloxyl units chosen from those of formulae (III) and (IV) below:

$$W'_aZ'_bSiO_{(4-(a+b))/2} \quad (III)$$

wherein:

the symbols W' represent a hydroxyl group (—OH), the symbols Z', which may be identical or different, each represent a monovalent hydrocarbon-based group chosen from alkyl groups having from 1 to 8 carbon atoms inclusive, such as methyl, ethyl, propyl and 3,3,3-trifluoropropyl groups, cycloalkyl groups, such as cyclohexyl, cycloheptyl and cyclooctyl groups, and aryl groups such as xylyl, tolyl and phenyl groups, and the symbol a is equal to 1 or 2, preferably equal to 1, the symbol b is equal to 0, 1 or 2 and the sum a+b is equal to 1, 2 or 3, and optionally units of formula below:

$$Z'_cSiO_{(4-c)/2} \quad (IV)$$

wherein Z' has the same meaning as above and the symbol c is equal to 0, 1, 2 or 3, and with the proviso that at least one of the units (III) or (IV) is a unit T or Q.

The silicone resin M which has hydroxyl groups and which is free of alkenyl or hydrosilyl SiH groups is a silicone resin comprising hydroxyl functions (—OH) with Z' being a $C_1$ to $C_8$ alkyl group. Examples of R' groups are the groups: methyl, ethyl, propyl, butyl, etc. These organosilicon resins are prepared by cohydrolysis and cocondensation of chlorosilanes. These resins are well-known and commercially available branched organopolysiloxane oligomers or polymers. They have, in their structure, at least two different siloxyl units chosen from those of the formula $(Z')_3SiO_{1/2}$ (unit M), $(Z')_2SiO_{2/2}$ (unit D), $Z'SiO_{3/2}$ (unit T) and $SiO_{4/2}$ (unit Q), at least one of these units being a unit T or Q. The symbols Z' have the same definition as above. These resins are not completely condensed and they have a weight content of hydroxyl groups of between 0.2% and 10% by weight or a weight content of hydroxyl groups of between 5 and 500 meq/100 g of resin.

According to another particular embodiment of the invention, the silicone resin M is present in the composition X at a content between 1% and 45% by weight relative to the total weight of the composition X, preferably between 2% and 45% by weight relative to the total weight of the composition X and even more preferably between 2% and 35% by weight relative to the total weight of the composition X.

The flexible polyurethane film can be produced from blown molten polyurethane.

Preferentially, a transparent or translucent flexible polyurethane film is used. When the adhesive item is of use as a dressing, the use of a transparent or translucent film has the advantage that it makes it possible to observe the wound, the injury or the site of entry of a catheter on which the dressing must be centered.

Preferably, said support S is a flexible polyurethane film having a thickness of from 5 to 600 µm, preferably from 5 to 250 µm and more preferentially from 10 to 100 µm.

As an example of a flexible polyurethane film, mention may be made of those which are used in the dressings sold by the company Smith & Nephew under the trademark Opsite®, or by the company 3M under the trademark Tegaderm® or else by the Laboratoires URGO under the trademark Optiskin®. These dressings consist of a transparent polyurethane thin film (of about from 20 to 50 µm) that has been made adhesive. Their transparency allows the area to be treated to be visually checked.

As another example of a flexible polyurethane film, mention may also be made of those sold under the trademarks Platilon® sold by the company Bayer MaterialScience and Inspire® sold by the company Coveris Advanced Coatings.

According to one preferred embodiment, the support S is a continuous flexible film which is permeable to air and impermeable to fluids.

The film can have a moisture vapor transmission rate (MVTR) that is variable depending on the intended application. A technique for measuring the moisture vapor transmission rate in liquid contact is described in standard NF-EN 13726-2. Preferably, the flexible polyurethane film will be chosen so as to obtain a dressing having a moisture vapor transmission rate (MVTR) greater than 300 g/m$^2$/24 hours, preferably greater than or equal to 600 g/m$^2$/24 hours, more preferably greater than or equal to 1000 g/m$^2$/24 hours.

According to another particular embodiment, the invention relates to a skin-adhesive item characterized in that the support S, which is a continuous flexible polyurethane film, comprises, on at least one part of the bottom face S2, a pressure-sensitive adhesive. According to one advantageous variant of the invention, the continuous flexible polyurethane film is perforated so as to be able to promote exudate circulation.

Thus, the adhesive item according to the invention is, according to one particular embodiment, a removable adhesive laminate and has the advantage of being able to be used as a layer of contact with the skin in various types of dressings.

The pressure-sensitive adhesive may be any of the numerous pressure-sensitive adhesives known from the art. These adhesives, generally in an anhydrous and solvent-free form, are permanently sticky at ambient temperature and adhere firmly to a variety of dissimilar surfaces during simple contact, without the need to use more than the pressure of a finger or of the hand. They do not require activation with water, a solvent or heat in order to have a strong adhesive holding force. Examples of pressure-sensitive adhesives comprise rubber/resin adhesives, which are mixtures of rubber material and of hard resin, and acrylic (or acrylate) adhesives. The pressure-sensitive adhesive class that is currently preferred for use in the present invention is that of acrylic adhesives.

According to one particular embodiment, the support S is a perforated flexible polyurethane film or a continuous flexible polyurethane film having a top face S1 and a bottom face S2 and which is impermeable to air and to fluids in its parts between the perforations.

In this particular embodiment, it is advantageous for the perforations of the support S to be circular and have a diameter from 50 μm to 10 mm.

According to another particular embodiment, the skin-adhesive item according to the invention is characterized in that it comprises one or more layers N comprising an absorbent body O, optionally separated by one or more intermediate layers P, placed on the support S on the side of the bottom face S2 of the support S. Preferably, the absorbent body O is chosen from the group made up of: a hydrophilic foam, a fabric pad, a hydrogel, a hydrocolloid and an alginate. Preferably, the absorbent body O is a polyurethane foam.

The layer D1 is made up of a silicone gel E obtained by crosslinking a crosslinkable silicone composition Y by means of a hydrosilylation reaction. The silicone gels are commonly used in the medical field, either for external use (breast prostheses, medical mattresses or cushions) or for internal use (breast implants placed in situ, dressings). They can be easily handled and have good mechanical properties, their density being close to that of human tissues. For the purposes of the present invention, the expression "silicone gel" denotes a crosslinked silicone product characterized in particular by a degree of penetration (or "penetrability") of between 50 and 500 tenths of 1 mm and preferably between 80 and 300 tenths of 1 mm (measured by penetrometry NF ISO 2137, Petrotest penetrometer, model PNR 12, weight of the rod and of the cone: 62.5 g). The cone-penetrability of a silicone gel is determined at 25° C. by measuring the depth of penetration of the cone into the sample, said depth being obtained by releasing the cone assembly of the penetrometer and leaving the cone to act for 5 s. The silicone gel has a cohesion such that it does not leave residues on the skin. It can be prepared from precursors of silicones which crosslink after they have been brought into contact according to a hydrosilylation reaction. Such systems are known from the prior art, for example in documents EP-A-0 251 810, EP-A-0 300 620 or U.S. Pat. No. 4,921,704. The compositions described are in two-component form and the crosslinking is carried out after mixing two parts called A and B. The mixtures of precursors described in these documents comprise essentially:

a part A which comprises a polydimethylsiloxane substituted with at least two vinyl groups, usually located at each of its ends, and a platinum catalyst, and a part B which comprises a polydimethylsiloxane having at least two hydrosilane groups and usually at least three hydrosilane groups.

The bringing together of the two parts causes, in the presence of the platinum catalyst, a crosslinking reaction (by means of a polyaddition reaction and in particular a hydrosilylation reaction) of the two functionalized polydimethylsiloxanes, which advantageously occurs at ambient temperature and can be accelerated by heat. Additives such as pigments, inhibitors or bulking fillers can be incorporated into at least one of the two parts. Examples of precursor compositions of the adhesive silicone gel can be chosen from the following products: Silbione® HC2 2011 A&B, Silbione® HC2 2031 A&B, Silbione® HC2 2022 A&B, Silbione® RT Gel 4642 A&B, Silbione® RT Gel 4712 A&B, Silbione® RT Gel 4317 A&B and Silbione® RT Gel 4717 A&B from the company Bluestar Silicones, those of the range Silpuran® from Wacker-Chemie GmbH, Nusil® MED-6340, Nusil® MED-6345 from Nusil Technology, and Dow Corning® MG 7-9800®, Dow Corning® MG 7-9850, Dow Corning® MG 7-9900® Soft Skin Adhesives Parts A&B from Dow Corning Corp.

Preferably, the amounts of silicone gel will be determined so as to obtain coatings having a silicone gel content of between 20 and 500 g/m$^2$ of support, preferably between 40 and 250 g/m$^2$ and even more preferentially between 80 and 350 g/m$^2$.

Preferably, the silicone gel E is prepared by crosslinking a silicone composition K comprising:

at least one organopolysiloxane G having on average, per molecule, two alkenyl groups, each bonded to a silicon atom, said alkenyl groups each having 2 to 6 carbon atoms and no silicon atom being bonded to more than just one alkenyl group, at least one hydrogenated compound of silicon H having, per molecule, at least two and preferably at least three hydrogen atoms, each bonded to a silicon atom, optionally at least one nonfunctionalized organopolysiloxane I and a platinum-based hydrosilylation catalyst J.

In general, the organopolysiloxane G contains on average two alkenyl groups bonded to silicon per molecule, each alkenyl group being bonded to a different silicon atom. The organopolysiloxane G is a substantially linear polymer, although a low degree of branching may exist. Preferably, the alkenyl groups are attached to silicon atoms, and they are preferably attached to the end silicon atoms of the siloxane chain. The alkenyl groups have at most 6 carbon atoms and they may for example be vinyl, allyl or hexenyl groups, although they are preferably vinyl groups. The remaining organic substituents of the organopolysiloxane G are chosen from alkyl and aryl groups, which are preferably alkyl groups having not more than 8 carbon atoms, and phenyl groups. Examples of these remaining substituents are the methyl, ethyl, propyl, isobutyl and phenyl groups. The most readily used are α,ω-(dimethylvinylsiloxy)-substituted polydimethylsiloxanes or polyorganosiloxanes of poly(dimethylsiloxy) (methylvinylsiloxy) α,ω-(dimethylvinylsiloxy)-substituted type.

The organopolysiloxane G is a commercial product, for instance the products of the Bluesil® 621V range from the company Bluestar Silicones, and are widely disclosed both with regard to their structures and with regard to their syntheses in the technical literature.

Preferably, the polyorganosiloxane G is linear or substantially linear and has a dynamic viscosity of less than or equal to 200 000 mPa·s, preferably less than or equal to 170 000 mPa·s and even more preferentially between 20 and 165 000 mPa·s.

According to another variant, the % by weight of reactive alkenyl groups directly bonded to a silicon atom is between 0.025% and 3%.

The hydrogenated compound of silicon H is generally a polyorganosiloxane, or a silane, comprising, per molecule, at least two, preferably three, hydrogen atoms bonded to silicon. These hydrogen atoms can be located on end siloxane units and also on siloxane units which are in the polymer chain, or else they can be located only in the siloxane chain.

In practice, the polyorganohydrosiloxanes H used are for example polyorganosiloxanes of poly(dimethylsiloxy)-(siloxymethylhydro)-α,ω-(dimethylhydro-siloxy)-substituted type or α,ω-(dimethylhydrosiloxy)-substituted polydimethylsiloxanes. They are commercial products and are widely disclosed both with regard to their structures and with regard to their syntheses in the technical literature.

The catalyst J has the same definition as the catalyst C set out above. For the catalyst J, the expression "effective amount of at least one hydrosilylation reaction catalyst" is intended to mean the amount sufficient to initiate the hydrosilylation reaction. With regard to the catalytically effective amount to be used, it goes without saying that those skilled in the art in the field in question are perfectly capable of determining the optimal amount of catalyst for promoting the hydrosilylation reaction. This amount depends in particular on the nature of the catalyst and of the organopolysiloxanes in question. To be specific, it can be indicated that it will be between 0.001% and 0.5% by weight relative to the total weight of the composition.

Preferably, the amounts of the constituents G and H are chosen such that the molar ratio r of the silicon-bonded hydrogen atoms to the silicon-bonded alkenyl radicals (X) is between 0.5:1 and 2:1.

As regards the preparation of the gel, it can be specified that the crosslinking of the composition into a gel is carried out at ambient temperature or after heating at temperatures of between 50 and 200° C. for example. In this context, the required crosslinking times are, for example, a few minutes.

These products are widely circulated and described commercially and are well known to those skilled in the art.

The protective layer F consisting of a peel-off protective material can consist of one or more parts that can be peeled off before use. This protective layer preferably covers the entire surface of the dressing and may be made of any material commonly used as protection by those skilled in the art in the dressings field. It may for example be in the form of a film, for example a polyolefin film such as polyethylene or polypropylene, or a polyester film. This film can advantageously be treated on at least one of its faces with a silicone compound such as a silane, a fluoro compound, or a silicone and fluoro compound. The choice of the material is generally adjusted to the nature of the silicone gel. The protective layer F consisting of a peel-off protective material preferably has a thickness of between 10 and 100 μm, for example of about 50 μm.

According to another embodiment of the invention, the skin-adhesive item according to the invention is characterized in that:
the support S is a perforated flexible polyurethane film, having a top face S1 and a bottom face S2,
the tie primer C1 is on the top face S1 of said support S and has been applied discontinuously so as to avoid blocking of the perforations of the support S, and
the layer D1 made up of a silicone gel E has been applied discontinuously so as to prevent blocking of the perforations of the support S.

A technique for preventing blocking of the perforations is known by those skilled in the art who may refer to patents EP-633758 or EP633757 which recommend the use of air (cold air or air at a temperature of less than or equal to 20° C.) which is blown over the bottom face of the perforated support so as to flow into the perforations of the support so as to flush the silicone compositions (before their crosslinking stage) which block the perforations. The temperature of the blown air is then increased so as to initiate the curing of the silicone compositions located just around the perforations. The support material is impermeable to air or sufficiently impermeable for substantially all the blown air to flow through the perforations. It is also possible to use a support material that allows the air to diffuse through it.

According to one particular embodiment, the skin-adhesive item according to the invention is characterized in that:
the tie primer C1 is applied on at least one part or on all of the top face S1 and on a part or on all of the bottom face S2 of said support S, and
at least one layer D1 made up of a silicone gel E obtained by crosslinking a crosslinkable silicone composition Y by means of a hydrosilylation reaction has been applied on said tie primer C1 present on the top face S1 and on the bottom face S2 of said support S.

Preferably, the thickness of the support S is between 5 and 200 μm, preferably between 10 and 75 μm.

According to one particular embodiment, the skin-adhesive item according to the invention is characterized in that it is a dressing for medical or paramedical use.

Another subject of the invention relates to a process for preparing a skin-adhesive item according to the invention and as described above, characterized in that it comprises:
a first step consisting in depositing, on said support S, sufficient amounts of the silicone composition X according to the invention and as described above and in crosslinking the silicone composition X, preferably at a temperature of between 60 and 200° C., for a sufficient time so as to form said tie primer C1, a second step consisting in depositing, on said tie primer C1, sufficient amounts of the silicone composition Y according to the invention and as described above and in crosslinking the silicone composition Y, preferably at a temperature between 60 and 200° C., for a sufficient time so as to form said layer D1.

According to one advantageous variant, the invention also relates to a process for preparing a skin-adhesive item according to the invention and as described above, characterized in that it comprises:

a step consisting in successively depositing, on said support S, sufficient amounts:
   of the silicone composition X according to the invention and as described above, and
   then subsequently of the silicone composition Y according to the invention and as described above on the silicone composition X,
then crosslinking said silicone compositions X and Y, preferably at a temperature of between 60 and 200° C., for a sufficient time so as to form said tie primer C1 and said layer D1.

Preferably, the amounts of the silicone composition X applied to the support S will be determined so as to obtain coatings having a content of silicone composition X before crosslinking of between 1 and 100 g/m² of support, preferably between 1 and 50 g/m² and even more preferentially between 2 and 30 g/m².

Preferably, the amounts of the composition Y will be determined so as to obtain coatings having a content of silicone gel E of between 20 and 500 g/m² of support, preferably between 40 and 250 g/m² and even more preferentially between 80 and 350 g/m².

As technique for depositing the compositions X and Y, mention may be made for example of the coating techniques carried out using a knife, in particular a knife-over-roll, a floating knife and a knife-over-blanket, or by padding, that is to say by squeezing between two rolls, or else by lick roll, rotary machine, reverse roll, transfer, spraying.

As other coating technique, mention may be made of the curtain coating technique. Curtain coating is a process for applying a coating liquid to an item or a support. Curtain coating is characterized by the formation of a freely falling curtain of a coating liquid which falls from the lip of the Hopper and, under gravity, encounters the item moving through the curtain so as to form a coat (or a coating). This technique has been widely used in the field of the preparation of multilayer photosensitive silver supports (see for example U.S. Pat. Nos. 3,508,947, 3,508,947 or EP537086).

It is known that the quality of the coat depends on the quality of the freely falling curtain. It is preferable for the curtain to have a stable laminar flow from the place where it forms to the line of encounter with the moving support. If this is not the case, the surface tension will lead the curtain to contract toward the interior and to interrupt the laminar flow. In order to prevent this problem, it is known practice to use edge guides to seize the freely falling curtain at its edges and to prevent it from contracting toward the interior owing to the surface tension. Examples of such systems are described in U.S. Pat. Nos. 4,933,215, 4,479,987, 4,974,533, 3,632,374, 4,479,987, EP537086 and U.S. Pat. No. 4,830,887.

The advantage of curtain coating is that it can enable the simultaneous coating of the silicone compositions X and Y according to the invention.

According to one advantageous embodiment, the process according to the invention is characterized in that, for said silicone composition X, the amounts by weight of the organopolysiloxanes A and B are determined such that the ratio RHalk=1 with RHalk=nH/tAlk and:
   nH=number of moles of hydrogen atom directly bonded to a silicon atom of the organopolysiloxane B, and
   tAlk=number of moles of alkenyl directly bonded to a silicon atom of the organopolysiloxane A.

This particular embodiment is particularly advantageous when successively deposited on said support S are sufficient amounts:
   of the silicone composition X according to the invention and as described above, and
   then subsequently of the silicone composition Y according to the invention and as described above on the silicone composition X, and
   the crosslinking step is then carried out.

This variant makes it possible to maintain a tack that is sufficiently high for the silicone gel E resulting from the coating and from the crosslinking of the silicone composition Y which is the precursor of the silicone gel.

The nonlimiting examples which follow show various possibilities of formulation of the compositions according to the invention and also the characteristics and the properties of the silicone gels obtained by crosslinking said compositions.

Another subject of the invention relates to a dressing or patch for medical or paramedical use, comprising the skin-adhesive item according to the invention and as described above.

EXAMPLES

The compositions described are in the two-component form. The crosslinking of the primer is carried out after mixing, at 25° C., two parts called Part A and Part B in a 50/50 ratio. The crosslinking of the Silbione® HC2 2022 gel in the examples below is carried out after mixing, at 25° C., two parts in a 50/50 ratio.

1) Starting Materials Used in the Composition of the Primer According to the Invention POS(A1)=poly(dimethylsiloxy)(methylvinylsiloxy) resin and containing tetravalent siloxyl units (units Q).

POS(A2)=α,ω-(dimethylvinylsiloxy)-substituted polydimethylsiloxane oil of viscosity 600 mPa·s.

POS(B)=α,ω-(dimethylhydrosiloxy)-substituted poly(dimethylsiloxy)(methylhydro-siloxy) oil of viscosity 25 mPa·s and containing 0.7% by weight of group H.

(C)=platinum organometallic complex used as catalyst of the reaction (D)=inhibitor of the hydrosilylation reaction of α-acetylenic alcohol type (K)=stabilizer of the mixture.

2) Table 1 Describes the Concentrations of Each of these Constituents in the Part a+Part B Mixtures Tested.

TABLE 1

| Constituents | Mixture A1 + B1 (comparative) | Mixture A2 + B2 (invention) | Mixture A3 + B3 (invention) | Mixture A4 + B4 (comparative) |
|---|---|---|---|---|
| POS(A1) | 52.32 | 52.13 | 50.21 | 43.23 |
| POS(A2) | 45.12 | 45.12 | 45.12 | 45.12 |
| POS(B) | 2.50 | 2.69 | 4.60 | 11.59 |
| (C) | 0.020 | 0.020 | 0.020 | 0.020 |
| (D) | 0.020 | 0.020 | 0.020 | 0.020 |
| (K) | 0.020 | 0.020 | 0.020 | 0.020 |
| RHalk | 0.96 | 1 | 1.8 | 5 |

2) Methods for Obtaining the Coatings Tested

Two different methods were monitored in order to test the above compositions as primer for improving the adhesion of the Silbione® HC2 2022 gel on a support which is a flexible polyurethane film.

Method for Coating the Primer then the Gel, without Prior Crosslinking of the Primer Application of the primer at a weight of between 5 and 15 g/m² to a support which is a flexible polyurethane film. The primer is applied to the film by means of a coating knife, then application of the Silbione® HC2 2022 gel at a weight of 200 g/m² by means of a coating knife, and crosslinking of the composite for 30 min at 120° C. in a ventilated oven.

Method for Coating the Primer then the Gel, with Prior Crosslinking of the Primer Application of the primer at a weight of between 5 and 15 g/m² to a support which is a flexible polyurethane film. The primer is applied to the film by means of a coating knife, then crosslinking of the primer for 5 min at 150° C. in a ventilated oven, then application of the Silbione® HC2 2022 gel at a weight of 200 g/m² by means of a coating knife, and crosslinking of the composite for 30 min at 120° C. in a ventilated oven.

3) Tests Carried Out on the Coatings

The two key properties tested in order to evaluate the efficiency of the primer are the adhesion of the primer or of the gel to the flexible polyurethane support and the adhesive capacity of the gel on the skin (tack). Indeed, when the adhesion of a silicone gel on a flexible polyurethane film is improved by the use of a primer, it is important to be sure that the adhesive capacity of the gel on the skin (tack) is preserved and that the adhesion of a medical device to the skin will not be modified by the use of a primer.

Evaluation of the Adhesive Capacity of the Silicone Gel on the Skin

The PROBE TACK Device (PT-1000) is the instrument used to evaluate the adhesive capacity of the gel coated. The test is carried out according to standard ASTM D2979 with the following test parameters:

surface area of contact with the adhesive: 0.2 cm², contact time with the adhesive: 1 s, contact pressure: 20 gf, speed of separation of the punch from the adhesive: 10 mm/s.

The energy for detachment from the substrate is expressed in mJ/cm².

Evaluation of the Adhesion of the Silicone Gel to the Support which is a Flexible Polyurethane Film The adhesion of the silicone gel to the support which is a flexible polyurethane film consists of a qualitative evaluation of the resistance of the gel during rub-off with a finger. The gel will be considered to be more adherent to the polyurethane film if the number of rub-offs is higher before observing delamination of the gel from its substrate.

4) Tables 2 and 3 Present the Application Properties Obtained as a Function of the Coating Method Used a) According to the method of coating the primer and then the gel, without prior crosslinking of the primer:

TABLE 2

|  | | With primer | | | |
| --- | --- | --- | --- | --- | --- |
|  | Without primer | Mixture A1 + B1 (comparative) | Mixture A2 + B2 (invention) | Mixture A3 + B3 (invention) | Mixture A4 + B4 (comparative) |
| Probe Tack (mJ/cm²) | 20 | 20 | 21 | 14 | 11 |
| Adhesion of the gel to polyurethane film (number of rub-offs with a finger) | 5 | 5 | >30 | >30 | >30 |

The gel coated onto primer according to this first process has:

a) good adhesion on a support which is a flexible polyurethane film, and b) satisfactory adhesion to the skin, insofar as the RHalk ratio of the primer is greater than or equal to 1 and less than or equal to 4.5.

The composition of the primer of which the RHalk ratio is equal to 1 (mixture A2+B2) provides a very good balance of properties (improvement of the adhesion of the silicone gel to the flexible polyurethane support, preservation of the adhesive capacity and the tack of the gel on the skin).

b) According to the method of coating the primer and then the gel, with prior crosslinking of the primer:

TABLE 3

|  | | With primer | | | |
| --- | --- | --- | --- | --- | --- |
|  | Without primer | Mixture A1 + B1 (comparative) | Mixture A2 + B2 (invention) | Mixture A3 + B3 (invention) | Mixture A4 + B4 (comparative) |
| Probe Tack (mJ/cm²) | 20 | 19 | 19 | 21 | 11 |
| Adhesion of the gel to polyurethane film (number of rub-offs with a finger) | 5 | 5 | 20 | >30 | >30 |

The gel coated onto primer according to this second process has:
a) good adhesion on a support which is a flexible polyurethane film, and
b) satisfactory adhesion to the skin, insofar as the RHalk ratio of the primer is greater than or equal to 1 and less than or equal to 4.5.

The composition of the primer of which the RHalk ratio is equal to 1.8 (mixture A3+B3) provides a very good balance of properties (improvement of the adhesion of the silicone gel to the flexible polyurethane support, preservation of the adhesive capacity, the tack and of the gel on the skin).

The invention claimed is:

1. A skin-adhesive item comprising:
a support S which is a flexible polyurethane film having a top face S1 and a bottom face S2,
at least one tie primer C1 applied to at least one part or to all of the top face S1 of the support S,
at least one layer D1 comprising a silicone gel E obtained by crosslinking a crosslinkable silicone composition Y by means of a hydrosilylation reaction, which has been applied to the at least one tie primer C1 facing the support S, and
optionally at least one protective layer F comprising of a peel-off protective material and applied to the at least one layer D1,
wherein the at least one tie primer C1 comprises a silicone elastomer which is not a silicone gel and which is obtained by crosslinking a silicone composition X comprising:
1) at least one organopolysiloxane A comprising, per molecule, at least two vinyl radicals each bonded to a silicon atom and comprising:
(i) at least two siloxy units of formula (A1):

$$Y_aZ_bSiO_{(4-(a+b))/2} \quad (A1)$$

wherein:
Y represents a C2 to C6 alkenyl group,
Z represents a monovalent hydrocarbon-based group chosen from alkyl groups having from 1 to 8 carbon atoms inclusive, cycloalkyl groups, and aryl groups,
a and b represent integers, a being 1, 2 or 3, b being 0, 1 or 2 and (a+b) being 1, 2 or 3;
(ii) and optionally comprising other siloxy units of formula (A2):

$$Z_cSiO_{(4-c)/2} \quad (A2)$$

wherein:
Z has the same meaning as above, and
c represents an integer which is 0, 1, 2 or 3;
2) at least one organopolysiloxane B comprising, per molecule, at least three hydrogen atoms each bonded to a silicon atom and comprising:
(i) at least three siloxy units of formula (B1):

$$HZ_bSiO_{(3-b)/2} \quad (B1)$$

wherein:
H is a hydrogen atom,
Z represents a monovalent hydrocarbon-based group chosen from alkyl groups having from 1 to 8 carbon atoms inclusive, cycloalkyl groups, and aryl groups,
b is 0, 1 or 2;

(ii) and optionally comprising other siloxy units of formula (B2):

$$Z_cSiO_{(4-c)/2} \quad (B2)$$

wherein:
Z has the same meaning as above, and
c represents an integer which is 0, 1, 2, or 3;
3) at least one hydrosilylation catalyst C;
4) at least one hydrosilylation reaction inhibitor D;
5) optionally at least one stabilizing additive K; and
6) optionally at least one silicone resin M which has hydroxyl groups and is free of alkenyl or hydrosilyl SiH groups, and
with the proviso that the amounts by weight of the organopolysiloxanes A and B are determined such that the RHalk=nH/tAlk ratio is 1.00≤RHalk≤4.5 with:
nH=number of moles of hydrogen atom directly bonded to a silicon atom of the organopolysiloxane B, and
tAlk=number of moles of alkenyl directly bonded to a silicon atom of the organopolysiloxane A.

2. The skin-adhesive item as claimed in claim 1, wherein the amounts by weight of the organopolysiloxanes A and B are determined such that 1.50≤RHalk≤4.0.

3. The skin-adhesive item as claimed in claim 1, wherein the silicone composition X comprises at least two organopolysiloxanes A as claimed in claim 1, and wherein at least one is a silicone resin A1 comprising:
(i) at least two siloxy units of formula (A1):

$$Y_aZ_bSiO_{(4-(a+b))/2} \quad (A1)$$

wherein:
Y represents a $C_2$ to $C_6$ alkenyl group,
Z represents a monovalent hydrocarbon-based group chosen from alkyl groups having from 1 to 8 carbon atoms inclusive, cycloalkyl groups, and aryl groups,
a and b represent integers, a being 1, 2 or 3, b being 0, 1 or 2 and (a+b) being 1, 2 or 3;
(ii) and other siloxy units of formula (A2):

$$Z_cSiO_{(4-c)/2} \quad (A2)$$

wherein:
Z has the same meaning as above,
c represents an integer which is 0, 1, 2 or 3; and
with the proviso that at least one siloxy unit (A2) has the formula $SiO_{4/2}$.

4. The skin-adhesive item as claimed in claim 3, wherein the silicone resin A1 has the formula $MD^{Vi}Q$ wherein:
M is a monovalent siloxyl unit of formula $R_3SiO_{1/2}$
$D^{Vi}$ is a divalent siloxyl unit of formula $RXSiO_{2/2}$, and
Q is a tetravalent siloxyl unit of formula $SiO_{4/2}$,
with the radical X corresponding to a vinyl group, and
the radical R corresponding to a monovalent hydrocarbon-based group chosen from alkyl groups having from 1 to 8 carbon atoms inclusive, cycloalkyl groups and aryl groups.

5. The skin adhesive item as claimed in claim 3, wherein Y is a vinyl group.

6. The skin adhesive item as claimed in claim 3, wherein when Z is an alkyl group, the alkyl group is a methyl, ethyl, propyl or 3,3,3 trifluoropropyl group.

7. The skin adhesive item as claimed in claim 3, wherein when Z is a cycloalkyl group, the cycloalkyl group is a cyclohexyl, cycloheptyl or cyclooctyl group.

8. The skin adhesive item as claimed in claim 3, wherein when Z is an aryl group, the aryl group is a xylyl, tolyl or phenyl group.

9. The skin adhesive item as claimed in claim 3, wherein a=1.

10. The skin adhesive item as claimed in claim 3, wherein when Z is an alkyl group, the alkyl group is a methyl, ethyl, propyl or 3,3,3 trifluoropropyl group.

11. The skin adhesive item as claimed in claim 3, wherein when Z is a cycloalkyl group, the cycloalkyl group is a cyclohexyl, cycloheptyl or cyclooctyl group.

12. The skin adhesive item as claimed in claim 3, wherein when Z is an aryl group, the aryl group is a xylyl, tolyl or phenyl group.

13. The skin-adhesive item as claimed in claim 1, wherein the support S is a continuous flexible polyurethane film which is permeable to air and impermeable to fluids.

14. The skin-adhesive item as claimed in claim 1, wherein the support S, which is a flexible polyurethane film, comprises, on at least one part of the bottom face S2, a pressure-sensitive adhesive.

15. The skin-adhesive item as claimed in claim 1, wherein the support S is a perforated flexible polyurethane film or a continuous flexible polyurethane film which has a top face S1 and a bottom face S2 and which is impermeable to air and fluids in its parts between the perforations.

16. The skin-adhesive item as claimed in claim 15, wherein the perforations of the support S are circular and have a diameter of from about 50 μm to about 10 mm.

17. The skin-adhesive item as claimed in claim 16, wherein the item comprises one or more layers N comprising an absorbent body O, optionally separated by one or more intermediate layers P, placed on the support S on the side of the bottom face S2 of the support S.

18. The skin-adhesive item as claimed in claim 17, wherein the absorbent body O is selected from the group consisting of: a hydrophilic foam, a fabric pad, a hydrogel, a hydrocolloid and an alginate.

19. The skin-adhesive item as claimed in claim 1, wherein:
the support S is a perforated flexible polyurethane film, having a top face S1 and a bottom face S2,
the at least one tie primer C1 is on the top face S1 of the support S and has been applied discontinuously so as to prevent blocking of the perforations of the support S, and
the at least one layer D1 comprising a silicone gel E has been applied discontinuously so as to prevent blocking of the perforations of the support S.

20. The skin-adhesive item as claimed in claim 1, wherein:
the at least one tie primer C1 is applied on at least one part or on all of the top face S1 and on a part or on all of the bottom face S2 of the support S, and
the at least one layer D1 comprising a silicone gel E obtained by crosslinking a crosslinkable silicone composition Y by means of a hydrosilylation reaction has been applied on said tie primer C1 present on the top face S1 and on the bottom face S2 of said support S.

21. The skin-adhesive item as claimed in claim 1, wherein the thickness of the support S is between about 5 μm and about 200 μm.

22. The skin-adhesive item as claimed in claim 21, wherein the thickness is between about 10 μm and about 75 μm.

23. The skin-adhesive item as claimed in claim 1, wherein the item is prepared as a dressing for medical or paramedical use.

24. A process for preparing a skin-adhesive item as described in claim 1, wherein the process comprises:
a first step of depositing, on said support S, sufficient amounts of the silicone composition X, and crosslinking the silicone composition X for a sufficient time so as to form the at least one tie primer C1,
a second step of depositing, on the at least one tie primer C1, sufficient amounts of the silicone composition Y and crosslinking the silicone composition Y, for a sufficient time so as to form the at least one layer D1.

25. The process as claimed in claim 24, wherein the crosslinking of silicone composition X in the first step is performed at from about 60° C. to about 200° C.

26. The process as claimed in claim 24, wherein the crosslinking of silicone composition Y in the second step is performed at from about 60° C. to about 200° C.

27. A process for preparing a skin-adhesive item of claim 1, wherein the process comprises:
successively depositing, on said support S, sufficient amounts:
of the silicone composition X,
then subsequently the silicone composition Y on the silicone composition X,
then crosslinking the silicone compositions X and Y for a sufficient time so as to form the at least one tie primer C1 and the at least one layer D1.

28. The process as claimed in claim 27, wherein, for the silicone composition X, the amounts by weight of the organopolysiloxanes A and B are determined such that the ratio RHalk=1 with RHalk=nH/tAlk and:
nH=number of moles of hydrogen atom directly bonded to a silicon atom of the organopolysiloxane B, and
tAlk=number of moles of alkenyl directly bonded to a silicon atom of the organopolysiloxane A.

29. The process as claimed in claim 27, wherein the crosslinking of silicone composition X and Y is performed at from about 60° C. to about 200° C.

30. The skin adhesive item as claimed in claim 1, wherein the alkenyl group Y is a vinyl group.

31. The skin adhesive item as claimed in claim 1, wherein when Z is an alkyl group, the alkyl group is a methyl, ethyl, propyl or 3,3,3 trifluoropropyl group.

32. The skin adhesive item as claimed in claim 1, wherein when Z is a cycloalkyl group, the cycloalkyl group is a cyclohexyl, cycloheptyl or cyclooctyl group.

33. The skin adhesive item as claimed in claim 1, wherein when Z is an aryl group, the aryl group is a xylyl, tolyl or phenyl group.

* * * * *